United States Patent
Loeffler et al.

(10) Patent No.: US 7,300,914 B2
(45) Date of Patent: *Nov. 27, 2007

(54) PROCESS FOR THE PREPARATION OF STABLE POLYMER CONCENTRATES

(75) Inventors: Matthias Loeffler, Niedernhausen (DE); Roman Morschhaeuser, Mainz (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 389 days.

This patent is subject to a terminal disclaimer.

(21) Appl. No.: 10/817,399

(22) Filed: Apr. 2, 2004

(65) Prior Publication Data

US 2004/0259759 A1 Dec. 23, 2004

(30) Foreign Application Priority Data

Apr. 3, 2003 (DE) ................. 103 15 184

(51) Int. Cl.
*C11D 3/37* (2006.01)
*C11D 3/43* (2006.01)
*C08F 291/00* (2006.01)

(52) U.S. Cl. ............ 510/475; 510/495; 510/499; 525/243; 525/296; 526/288; 526/303.1; 526/307.1; 526/307.2

(58) Field of Classification Search ........ 510/475, 510/495, 499; 525/243, 296; 526/288, 303.1, 526/307.1, 307.2

See application file for complete search history.

(56) References Cited

U.S. PATENT DOCUMENTS

| 5,104,645 | A | 4/1992 | Cardin et al. |
|---|---|---|---|
| 6,355,752 | B1 | 3/2002 | Brungs et al. |
| 6,437,068 | B2 | 8/2002 | Loffler et al. |
| 6,506,833 | B2 | 1/2003 | Loeffler et al. |
| 6,683,144 | B2 | 1/2004 | Loeffler et al. |
| 2004/0063886 | A1 | 4/2004 | Loeffler et al. |
| 2004/0109836 | A1 | 6/2004 | Loeffler et al. |
| 2004/0109838 | A1* | 6/2004 | Morschhuser et al. ... 424/70.16 |

FOREIGN PATENT DOCUMENTS

| CA | 2209060 A1 | | 12/1997 |
|---|---|---|---|
| DE | 19625810 | | 1/1998 |
| EP | 816403 | | 1/1998 |
| EP | 1028129 | | 8/2000 |
| EP | 1116733 | | 7/2001 |
| EP | WO 02/44230 | * | 6/2002 |
| WO | WO0244231 | | 6/2002 |

* cited by examiner

*Primary Examiner*—Brian Mruk
(74) *Attorney, Agent, or Firm*—Tod A. Waldrop

(57) ABSTRACT

Process for preparing stable polymer concentrates, wherein acryloyldimethyltaurine and/or acryloyldimethyltaurate are free-radically polymerized with at least one further component in the presence of a polymerization medium, a higher-boiling solvent or solvent mixture is added to the resulting reaction product or reaction mixture, and the lower-boiling polymerization medium is removed, optionally under reduced pressure.

21 Claims, No Drawings

PROCESS FOR THE PREPARATION OF STABLE POLYMER CONCENTRATES

The present invention relates to a process for preparing concentrates comprising polymers based on acryloyldimethyltaurine and its salts, obtainable by polymerizing acryloyldimethyltaurine and/or acryloyldimethyltaurates in the presence of one or more olefinic comonomers, polymeric additives and components having functional groups.

The application WO 02/44231 describes a novel class of polymers based on acryloyldimethyltaurine or its salts. These polymers cover a broad range of performance properties and may be used as thickeners, bodying agents, emulsifiers, dispersants, lubricants, conditioners and/or stabilizers in cosmetic, dermatological and pharmaceutical compositions.

The copolymers based on acryloyldimethyltaurine or its salts, prepared preferably by precipitation polymerization, according to the prior art are pulverulent substances having performance disadvantages resulting therefrom. Pulverulent substances harbor the fundamental risk of a dust explosion, and the storage stability of the powders is additionally impaired by hygroscopicity.

For the processing and use of the pulverulent products, the dissolution procedure (preference is given to incorporating the polymers into aqueous media) is usually very time-consuming. The dissolution procedure of the pulverulent components may, depending on the batch size, take one hour or more. In addition, incomplete dissolution/swelling of the pulverulent products is frequently observed, which leads to a reduction in the quality and stability of the end formulation (lump formation). In addition, special stirring and dispersing apparatus is generally required in the processing and use of the pulverulent products, in order to dissolve or to disperse the polymers of acryloyldimethyltaurine or its salts in the compositions.

A further problem arises in the preparation of hydrophobically modified polymers having a high fraction of hydrophobic side chains. As soon as the proportion by weight of the hydrophobic side chains exceeds a critical value (typically >50% by weight), an isolation of the resulting polymers can only be realized with difficulty as a consequence of the amorphous, waxlike consistency. This means that a precipitation polymerization is also ruled out in this case as a consequence of the solubility in organic solvents.

It is an object of the present invention to develop a one-pot process for preparing polymer concentrates comprising polymers based on acryloyldimethyltaurine or its salts in highly concentrated liquid or liquid-disperse form having a very high polymer content and low viscosity with simultaneously high stability of the solution or dispersion in a cosmetically and pharmaceutically acceptable matrix.

It has been found that, surprisingly, storage-stable and thermally stable concentrates may be prepared from polymers described below containing units of acryloyldimethyltaurine or its salts by adding, after the polymerization reaction, a solvent whose boiling point is higher than the boiling point of the polymerization medium or solvent used for the polymerization, and subsequently removing the lower-boiling polymerization medium or solvent, optionally at a pressure which is reduced compared to atmospheric pressure, and optionally at a temperature which is elevated compared to room temperature (25°).

The present invention provides a process for preparing a concentrate in liquid or liquid-disperse form, comprising I) from 5 to 80% by weight, preferably from 20 to 60% by weight, more preferably from 30 to 40% by weight, of a polymer obtainable by free-radically polymerizing acryloyldimethyltaurine and/or acryloyldimethyltaurates [component A)] in the presence of one or more substances selected from one or more of the components D) to G), and optionally additionally in the presence of one or more further substances, component D) consisting of at least monofunctional silicon-containing substances capable of free-radical polymerization, E) consisting of at least monofunctional fluorine-containing substances capable of free-radical polymerization, F) consisting of olefinically mono- or polyunsaturated, optionally crosslinking macromonomers which each have at least one oxygen, nitrogen, sulfur or phosphorus atom and a number-average molecular weight greater than or equal to 200 g/mol, the macromonomers not being silicon-containing substances as per component D) or fluorine-containing substances as per component E), and G) consisting of polymeric additives having number-average molecular weights of from 200 g/mol to $10^9$ g/mol, II) from 20 to 95% by weight, preferably from 30 to 80% by weight, more preferably from 40 to 60% by weight, of an organic solvent or solvent mixture, III) from 0 to 60% by weight of an emulsifier, preferably 0% by weight of emulsifier, for polymer concentrates having a high fraction of hydrophobic side chains and preferably from 5 to 40% by weight, more preferably from 10 to 20% by weight, of an emulsifier for polymer concentrates having a low fraction of hydrophobic side chains, and IV) from 0 to 30% by weight, preferably from 0 to 10% by weight, more preferably from 0 to 5% by weight, of water, which comprises a) effecting the polymerization of acryloyldimethyltaurine and/or acryloyldimethyltaurates in the presence of at least one substance or a plurality of substances selected from one or more of the components D) to G) and optionally in the presence of one or more further substances by a free-radical polymerization reaction, preferably by solution polymerization, gel polymerization, by an emulsion process, precipitation process, high pressure process or suspension process, in a polymerization medium which behaves very substantially inertly with respect to free-radical polymerization reactions and permits the formation of high molecular weights, preferably water and lower, tertiary alcohols or hydrocarbons having from 3 to 30 carbon atoms, more preferably t-butanol, b) adding a higher-boiling solvent or solvent mixture, and also optionally emulsifier and/or water to the mixture of polymer and polymerization medium obtained from step a), the boiling point of the higher-boiling solvent added being at least 10° C. higher than that of the polymerization medium used for the polymerization, and c) removing the lower-boiling solvent or solvent mixture, optionally at a pressure which is reduced compared to atmospheric pressure and optionally at a temperature which is elevated compared to room temperature (25° C.).

The present invention further provides the concentrates which have been prepared by the process according to the invention.

The acryloyldimethyltaurates may be the inorganic or organic salts of acryloyldimethyltaurine (acrylamidopropyl- 2-methyl-2-sulfonic acid). Preference is given to the Li$^+$, Na$^+$, K$^+$, Mg$^{++}$, Ca$^{++}$, Al$^{+++}$ and/or NH$_4^+$ salts. Preference is likewise given to the monoalkylammonium, dialkylammonium, trialkylammonium and/or tetraalkylammonium salts, and the alkyl substituents of the amines may each independently be (C$_1$-C$_{22}$)-alkyl radicals or (C$_2$-C$_{10}$)-hydroxyalkyl radicals. Preference is also given to mono- to triethoxylated ammonium compounds having a differing degree of ethoxylation. Mixtures of two or more of the abovementioned representatives are likewise within the scope of the invention. The degree of neutralization of acryloyldimethyltaurine may be between 0 and 100%; particular preference is given to a degree of neutralization of above 80%.

Based on the total mass of the polymers, the content of acryloyldimethyltaurine or acryloyldimethyltaurates is at least 0.1% by weight, preferably from 20 to 99.5% by weight and more preferably from 50 to 98% by weight.

Suitable polymerizable silicon-containing substances of component D) are any at least monoolefinically unsaturated compounds which are capable of free-radical polymerization under the reaction conditions selected in each case. The distribution of the individual silicone-containing monomers over the polymer chains being formed does not necessarily have to be random. The formation of, for example, block (including multiblock) or gradient-like structures is also within the scope of the invention. Combinations of two or more different silicone-containing representatives are also possible. The use of silicone-containing substances having two or more polymerization-active groups leads to the construction of branched or crosslinked structures.

Preferred silicone-containing substances are those of the formula (I)

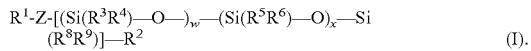

In this formula, R$^1$ is a polymerizable radical from the group of the vinylically unsaturated compounds which are suitable for constructing polymeric structures by a free-radical route. R$^1$ is preferably a vinyl, allyl, methallyl, methylvinyl, acryloyl (CH$_2$=CH—CO—), methacryloyl (CH$_2$=C[CH$_3$]—CO—), crotonyl, senecionyl, itaconyl, maleyl, fumaryl or styryl radical.

To bond the silicone-containing polymer chain to the reactive end group R$^1$, a suitable chemical bridge Z is required. Preferred bridges Z are —O—, —O—((C$_1$-C$_{50}$) alkylene)-, —O—((C$_6$-C$_{30}$)arylene)-, —O—((C$_5$-C$_8$)cycloalkylene)-, —O—((C$_1$-C$_{50}$)alkenylene)-, -(polypropylene oxide)$_n$-, -(polyethylene oxide)$_o$-, -(polypropylene oxide)$_n$-polyethylene oxide)$_o$-, where n and o are each independently numbers from 0 to 200, and the distribution of the EO/PO units may be random or in blocks. Also suitable as bridging moieties Z are

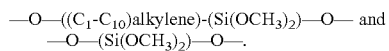

The polymeric middle section is represented by silicone-containing repeating units.

The R$^3$, R$^4$, R$^5$ and R$^6$ radicals are each independently —CH$_3$, —O—CH$_3$, —C$_6$H$_5$ or —O—C$_6$H$_5$.

The R$^8$ and R$^9$ radicals are each independently —CH$_3$, —O—CH$_3$, —C$_6$H$_5$, —O—C$_6$H$_5$ or —O—Si(CH$_3$)$_3$.

The indices w and x each represent stoichiometric coefficients which are each independently from 0 to 500, preferably from 10 to 250.

The distribution of the repeating units over the chain may not only be purely random, but also in blocks, alternating or gradient-like.

R$^2$ may either symbolize an aliphatic, olefinic, cycloaliphatic, arylaliphatic or aromatic (C$_1$-C$_{50}$)hydrocarbon radical (linear or branched) or be —OH, —NH$_2$, —N(CH$_3$)$_2$ or —R$^7$, or be the structural unit [-Z-R$^1$] where Z and R$^1$ are each as defined above. R$^7$ represents further Si-containing moieties. Preferred R$^7$ radicals are —O—Si(CH$_3$)$_3$, —O—Si(Ph)$_3$, —O—Si(O—Si(CH$_3$)$_3$)$_2$CH$_3$) and —O—Si(O—Si(Ph)$_3$)$_2$Ph). When R$^2$ is an element of the [-Z-R$^1$] group, the monomers are difunctional and may be used to crosslink the polymer structures being formed.

Formula (I) describes not only vinylically functionalized, silicone-containing polymer species having a distribution typical for a polymer, but also defined compounds having discrete molecular weights.

Particularly preferred silicone-containing substances are the following acrylically or methacrylically modified silicone-containing substances:

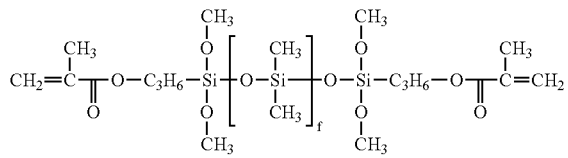

Methacryloxypropyldimethoxysilyl-endblocked polydimethylsiloxanes (f=from 2 to 500)

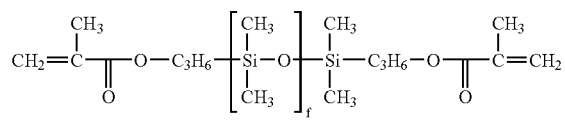

Methacryloxypropyl-endblocked polydimethylsiloxanes (f=from 2 to 500)

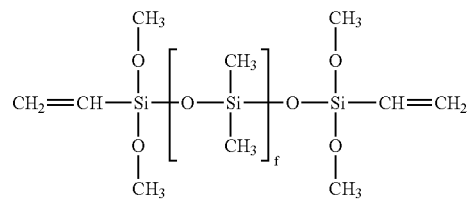

Vinyldimethoxysilyl-endblocked polydimethylsiloxanes (f=from 2 to 500)

Based on the total mass of the polymers, the content of silicon-containing components may be up to 99.9% by weight, preferably from 0.5 to 30% by weight, especially preferably from 1 to 20% by weight.

Suitable polymerizable, fluorine-containing substances of component E) are any at least monoolefinically unsaturated compounds which are capable of free-radical polymerization under the reaction conditions selected in each case. The distribution of the individual fluorine-containing monomers over the polymer chains being formed does not necessarily have to be random. The formation of, for example, block (including multiblock) or gradient-like structures is also within the scope of the invention. Combinations of two or more different, fluorine-containing substances of component E) are also possible, and it is clear to the expert that monofunctional representatives lead to the formation of comblike structures, whereas di-, tri-, or polyfunctional substances of component E) lead to at least part-crosslinked structures.

Preferred fluorine-containing substances of component E) are those of the formula (II).

In this formula, $R^1$ is a polymerizable function from the group of the vinylically unsaturated compounds which is suitable for constructing polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical, more preferably an acryloyl and methacryloyl radical.

To bond the fluorine-containing moiety to the reactive end group $R^1$, a suitable chemical bridge Y is required. Preferred bridges Y are —O—, —C(O)—, —C(O)—O—, —S—, —O—$CH_2$—CH(O—)—$CH_2$OH, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O—($C_1$-$C_{50}$)alkyl-O—, —O-phenyl-O—, —O-benzyl-O—, —O—($C_5$-$C_8$)cycloalkyl-O—, —O—($C_1$-$C_{50}$)alkenyl-O—, —O—(CH($CH_3$)—$CH_2$—O)$_n$—, —O—($CH_2$—$CH_2$—O)$_n$—, and —O—([CH($CH_3$)—-$CH_2$—O]$_n$—[$CH_2$—$CH_2$—O]$_m$)$_o$—, where n, m and o are each independently numbers from 0 to 200, and the distribution of the EO and PO units may be random or in blocks.

r and s are stoichiometrical coefficients which are each independently numbers from 0 to 200.

Preferred fluorine-containing substances of component E) of the formula (II) are perfluorohexylethanol methacrylate, perfluorohexoylpropanol methacrylate, perfluorooctylethanol methacrylate, perfluorooctylpropanol methacrylate, perfluorohexylethanolyl polyglycol ether methacrylate, perfluorohexoyl propanolyl poly[ethylglycol-co-propylene glycol ether] acrylate, perfluorooctylethanolyl poly[ethylglycol-blockco-propylene glycol ether] methacrylate, perfluorooctylpropanolyl polypropylene glycol ether methacrylate.

Based on the total mass of the polymers, the content of fluorine-containing components may be up to 99.9% by weight, preferably from 0.5 to 30% by weight, especially preferably from 1 to 20% by weight.

The macromonomers of component F) are at least monoolefinically functionalized polymers having one or more discrete repeating units and a number-average molecular weight greater than or equal to 200 g/mol. In the polymerization, mixtures of chemically different macromonomers of component F) may also be used. The macromonomers are polymeric structures which are composed of one or more repeating unit(s) and have a molecular weight distribution which is characteristic of polymers.

Preferred macromonomers of component F) are compounds of the formula (III).

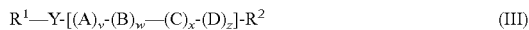

$R^1$ is a polymerizable function from the group of the vinylically unsaturated compounds which are suitable for forming polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

To bond the polymer chain to the reactive end group, a suitable bridging group Y is required. Preferred bridges Y are —O—, —C(O)—, —C(O)—O—, —S—, —O—$CH_2$—CH(O—)—$CH_2$OH, —O—$CH_2$—CH(OH)—$CH_2$O—, —O—$SO_2$—O—, —O—$SO_2$—O—, —O—SO—O—, —PH—, —P($CH_3$)—, —$PO_3$—, —NH— and —N($CH_3$)—, more preferably —O—.

The polymeric center moiety of the macromonomer is represented by the discrete repeating units A, B, C and D. Preferred repeating units A, B, C and D are derived from acrylamide, methacrylamide, ethylene oxide, propylene oxide, acryloyldimethyltaurine, acrylic acid, methacrylic acid, methyl methacrylate, acrylonitrile, maleic acid, vinyl acetate, styrene, 1,3-butadiene, isoprene, isobutene, diethylacrylamide and diisopropylacrylamide.

The indices v, w, x and z in the formula (III) represent the stoichiometric coefficients relating to the repeating units A, B, C and D. v, w, x, and z are each independently from 0 to 500, preferably from 1 to 30, although the sum of the four coefficients has to be on average $\geq 1$.

The distribution of the repeating units over the macromonomer chain may be random, block-like, alternating or gradient-like.

$R^2$ is a linear or branched aliphatic, olefinic, cycloaliphatic, arylaliphatic or aromatic ($C_1$-$C_{50}$) hydrocarbon radical, OH, —$NH_2$, —N($CH_3$)$_2$ or is the [—Y—$R^1$] structural unit. In the case that $R^2$ is [—Y—$R^1$], the macromonomers are difunctional and are suitable for crosslinking the copolymers.

Particularly preferred macromonomers of component F) are acrylically or methacrylically monofunctionalized alkyl ethoxylates of the formula (IV).

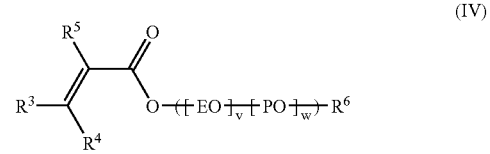

$R_3$, $R_4$, $R_5$ and $R_6$ are each independently hydrogen or n-aliphatic, isoaliphatic, olefinic, cycloaliphatic, arylaliphatic or aromatic ($C_1$-$C_{30}$) hydrocarbon radicals.

$R_3$ and $R_4$ are preferably each H or —$CH_3$, more preferably H. $R_5$ is preferably H or —$CH_3$. $R_6$ is preferably an n-aliphatic, isoaliphatic, olefinic, cycloaliphatic, arylaliphatic or aromatic ($C_1$-$C_{30}$) hydrocarbon radical. In a preferred embodiment, $R^6$ is preferably an alkyl radical having from 8 to 24 carbon atoms, especially preferably having from 12 to 22 carbon atoms.

v and w are in turn the stoichiometric coefficients relating to the ethylene oxide units (EO) and propylene oxide units (PO). v and w are each independently from 0 to 500, preferably from 1 to 30, although the sum of v and w on average has to be $\geq 1$. The distribution of the EO and PO units over the macromonomer chain may be random, block-like, alternating or gradient-like.

Further especially preferred macromonomers of component F) have the following structure in accordance with formula (IV):

| Name | $R^3$ | $R^4$ | $R^5$ | $R^6$ | v | w |
|---|---|---|---|---|---|---|
| Genapol ® LA-030 methacrylate | H | H | —$CH_3$ | -lauryl | 3 | 0 |
| Genapol ® LA-070 methacrylate | H | H | —$CH_3$ | -lauryl | 7 | 0 |

-continued

| Name | $R^3$ | $R^4$ | $R^5$ | $R^6$ | v | w |
|---|---|---|---|---|---|---|
| Genapol ® LA-200 methacrylate | H | H | —$CH_3$ | -lauryl | 20 | 0 |
| Genapol ® LA-250 methacrylate | H | H | —$CH_3$ | -lauryl | 25 | 0 |
| Genapol ® T-080 methacrylate | H | H | —$CH_3$ | -talc | 8 | 0 |
| Genapol ® T-080 acrylate | H | H | H | -talc | 8 | 0 |
| Genapol ® T-250 methacrylate | H | H | —$CH_3$ | -talc | 25 | 0 |
| Genapol ® T-250 crotonate | —$CH_3$ | H | —$CH_3$ | -talc | 25 | 0 |
| Genapol ® OC-030 methacrylate | H | H | —$CH_3$ | -octyl | 3 | 0 |
| Genapol ® OC-105 methacrylate | H | H | —$CH_3$ | -octyl | 10 | 5 |
| Genapol ® Behenyl-010 methacrylate | H | H | H | -behenyl | 10 | 0 |
| Genapol ® Behenyl-020 methacrylate | H | H | H | -behenyl | 20 | 0 |
| Genapol ® Behenyl-010 senecionyl | —$CH_3$ | —$CH_3$ | H | -behenyl | 10 | 0 |
| Genapol ® PEG-440 diacrylate | H | H | H | -acryl | 10 | 0 |
| Genapol ® B-11-50 methacrylate | H | H | —$CH_3$ | -butyl | 17 | 13 |
| Genapol ® MPEG-750 methacrylate | H | H | —$CH_3$ | -methyl | 18 | 0 |
| Genapol ® P-010 acrylate | H | H | H | -phenyl | 10 | 0 |
| Genapol ® O-050 acrylate | H | H | H | -oleyl | 5 | 0 |

Especially suitable as macromonomers of component F) are also esters of (meth)acrylic acid with
- ($C_{10}$-$C_{18}$) fatty alcohol polyglycol ethers having 8 EO units (Genapol® C-080)
- $C_{11}$ oxo alcohol polyglycol ethers having 8 EO units (Genapol® UD-080)
- ($C_{12}$-$C_{14}$) fatty alcohol polyglycol ethers having 7 EO units (Genapol® LA-070)
- ($C_{12}$-$C_{14}$) fatty alcohol polyglycol ethers having 11 EO units (Genapol® LA-110)
- ($C_{16}$-$C_{18}$) fatty alcohol polyglycol ethers having 8 EO units (Genapol® T-080)
- ($C_{16}$-$C_{18}$) fatty alcohol polyglycol ethers having 15 EO units (Genapol® T-150)
- ($C_{16}$-$C_{18}$) fatty alcohol polyglycol ethers having 11 EO units (Genapol® T-110)
- ($C_{16}$-$C_{18}$) fatty alcohol polyglycol ethers having 20 EO units (Genapol® T-200)
- ($C_{16}$-$C_{18}$) fatty alcohol polyglycol ethers having 25 EO units (Genapol® T-250)
- ($C_{18}$-$C_{22}$) fatty alcohol polyglycol ethers having 25 EO units and/or
- iso($C_{16}$-$C_{18}$) fatty alcohol polyglycol ethers having 25 EO units.

The Genapol® types are products from Clariant GmbH.

The molecular weight of the macromonomers of component F) is preferably from 200 g/mol to $10^6$ g/mol, more preferably from 150 to $10^4$ g/mol and especially preferably from 200 to 5 000 g/mol.

Based on the total mass of the polymers, suitable macromonomers may be used up to 99.9% by weight. The ranges finding use are preferably from 0.5 to 30% by weight and from 70 to 99.5% by weight. Particular preference is given to fractions of from 1 to 20% by weight and from 75 to 95% by weight.

When acryloyldimethyltaurine and/or acryloyldimethyltaurates are polymerized in the presence of further monomers capable of free-radical polymerization, this results in copolymers.

In a preferred embodiment, the polymerization is carried out in the presence of at least one polymeric additive of component G), in which case the additive of component G) is added to the polymerization medium fully or partly dissolved before the actual polymerization. The use of a plurality of additives of component G) is likewise in accordance with the invention. Crosslinked additives of component G) may likewise be used.

The additives of component G) or their mixtures merely have to be fully or partly soluble in the polymerization medium selected. During the actual polymerization step, the additive of component G) has a plurality of functions. Firstly it prevents the formation of overcrosslinked polymer fractions in the polymer forming in the actual polymerization step and secondly the additive of component G) is attacked randomly by active free radicals in accordance with the commonly known mechanism of graft copolymerization. This has the result that, depending on the additive of component G), larger or smaller fractions thereof are incorporated into the polymers. In addition, suitable additives of component G) have the property of changing the dissolution parameters of polymers forming during the free-radical polymerization reaction in such a way that the average molecular weights are shifted to higher values. Compared with similar polymers which have been prepared without the addition of the additives of component G), those which have been prepared with the addition of additives of component G) advantageously have a significantly higher viscosity in aqueous solution.

Preferred additives of components G) are homo- and copolymers which are soluble in water and/or alcohols, preferably in t-butanol. Copolymers refer to those having more than two different monomer types.

Particularly preferred additives of component G) are homo- and copolymers of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholine, hydroxyethyl methacrylate, diallyldimethylammonium chloride (DADMAC) and/or [2-(methacryloyloxy)ethyl]trimethylammonium chloride (MAPTAC); polyalkylene glycols and/or alkyl polyglycols.

Especially preferred additives of component G) are polyvinylpyrrolidone (e.g. Luviskol K15®, K20® and K30® from BASF), poly(N-vinylformamides), poly(N-vinylcaprolactams) and copolymers of N-vinylpyrrolidone, N-vinylformamide and/or acrylic acid which may also be partly or fully esterified.

The molecular weight of the additives of component G) is preferably from $10^2$ to $10^7$ g/mol, more preferably from $0.5*10^4$ to $10^6$ g/mol.

The use amount of the polymeric additive of component G) is, based on the total mass of the monomers to be polymerized in the polymerization, preferably from 0.1 to 90% by weight, more preferably from 1 to 20% by weight and especially preferably from 1.5 to 10% by weight.

The further substances which are present in the free-radical polymerization in addition to acryloyldimethyltaurine and/or acryloyldimethyltaurates and the substances selected from one or more of the components D) to G) are preferably further at least monofunctional comonomers capable of free-radical polymerization or polymeric additives.

These further substances are referred to hereinbelow as substances selected from component BC).

In a preferred embodiment, the substances of component BC) are selected from the comonomers of component B).

The comonomers of component B) which may be used are any olefinically unsaturated, noncationic monomers whose reaction parameters allow copolymerization with acryloyldimethyltaurine and/or acryloyldimethyltaurates in the particular reaction media.

In a particularly preferred embodiment, the comonomers of component B) are selected from olefinically unsaturated, noncationic, optionally crosslinking comonomers which have at least one oxygen, nitrogen, sulfur or phosphorus atom and a molecular weight of less than 500 g/mol.

Preferred comonomers of component B) are unsaturated carboxylic acids and their anhydrides and salts, and also esters with aliphatic, olefinic, cycloaliphatic, arylaliphatic or aromatic alcohols having a carbon number of from 1 to 30.

Particularly preferred unsaturated carboxylic acids are acrylic acid, methacrylic acid, styrenesulfonic acid, maleic acid, fumaric acid, crotonic acid, itaconic acid and senecic acid.

Preferred counterions are $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, and the alkyl substituents of the amines may each independently be $(C_1-C_{22})$alkyl radicals or $(C_2-C_{10})$hydroxyalkyl radicals. In addition, mono- to triethoxylated ammonium compounds having a differing degree of ethoxylation may find use. The degree of neutralization of the carboxylic acids may be between 0 and 100%.

Preferred comonomers of component B) are also openchain N-vinylamides, preferably N-vinylformamide (VIFA), N-vinylmethylformamide, N-vinylmethylacetamide (VIMA) and N-vinylacetamide; cyclic N-vinylamides (N-vinyllactams) having a ring size of from 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide and mono[2-(methacryloyloxy)ethyl] succinate; N,N-dimethylaminoethyl methacrylate; diethylaminomethyl methacrylate; acryloyl- and methacryloylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable as comonomers of component B) are inorganic acids and their salts and esters. Preferred acids are vinylphosphonic acid, vinylsulfonic acid, allylphosphonic acid and methallylsulfonic acid.

The proportion by weight of comonomers of component B), based on the total mass of the polymers, may be from 0 to 99.8% by weight and is preferably from 0.5 to 80% by weight, more preferably from 2 to 50% by weight.

In a further preferred embodiment, the substances of component BC) are selected from comonomers of component C).

Useful comonomers of component C) are any olefinically unsaturated monomers having cationic charge which are capable of forming copolymers in the selected reaction media with acryloyldimethyltaurine or its salts. The resulting distribution of the cationic charges over the chains may be random, alternating, block-like or gradient-like. The cationic comonomers of component C) also include those which bear the cationic charge in the form of a betaine, zwitterionic, or amphoteric structure.

In a particularly preferred embodiment, the comonomers of component C) are selected from olefinically unsaturated, cationic comonomers which have at least one oxygen, nitrogen, sulfur or phosphorus atom and a molecular weight of less than 500 g/mol.

Comonomers of component C) in the context of the invention are also amino-functionalized precursors which may be converted by polymer-like reactions to their corresponding quaternary (for example reaction with dimethyl sulfate, methyl chloride), zwitterionic (for example reaction with hydrogen peroxide), betaine (for example reaction with chloroacetic acid) or amphoteric derivatives.

Particularly preferred comonomers of component C) are diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride
N-methyl-4-vinylpyridinium chloride
dimethylaminoethyl methacrylate,
dimethylaminopropyl methacrylamide,
methacryloylethyl N-oxide and/or
methacryloylethylbetaine.

The proportion by weight of comonomers of component C) may, based on the total mass of the polymers, be from 0.1 to 99.8% by weight, preferably from 0.5 to 30% by weight and more preferably from 1 to 20% by weight.

In a further preferred embodiment, the inventive polymers are crosslinked, i.e. they contain comonomers having at least two polymerizable vinyl groups.

Preferred crosslinkers are methylenebisacrylamide; methylenebismethacrylamide; esters of unsaturated mono- and polycarboxylic acids with polyols, preferably diacrylates and triacrylates or methacrylates, more preferably butanediol and ethylene glycol diacrylate and methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives.

An especially preferred crosslinker is trimethylolpropane triacrylate (TMPTA).

The proportion by weight of crosslinking comonomers, based on the total mass of the polymers, is preferably up to 20% by weight, more preferably from 0.05 to 10% by weight and especially preferably from 0.1 to 7% by weight.

Preferred polymers are those which are obtainable by copolymerizing substances of at least components A), C) and D).

Preferred polymers are also those which are obtainable by copolymerizing substances of at least components A), C) and E).

Preferred polymers are also those which are obtainable by copolymerizing substances of at least components A), D) and F).

Preferred polymers are also those which are obtainable by copolymerizing substances of at least components A) and F).

Useful polymerization media may be any organic or inorganic solvents which behave very substantially inertly with respect to free-radical polymerization reactions and advantageously permit the formation of moderate or high molecular weights. Preference is given to using water; lower alcohols; preferably methanol, ethanol, propanols, iso-, sec- and t-butanol, especially preferably t-butanol; hydrocarbons having from 1 to 30 carbon atoms and mixtures of the aforementioned compounds.

The polymerization reaction is preferably effected within the temperature range between 0 and 150° C., more preferably between 10 and 100° C., either at atmospheric pressure or under elevated or reduced pressure. The polymerization may also optionally be performed under a protective gas atmosphere, preferably under nitrogen.

To induce the polymerization, high-energy electromagnetic beams, mechanical energy or the customary chemical polymerization initiators such as organic peroxides, e.g. benzoyl peroxide, tert-butyl hydroperoxide, methyl ethyl ketone peroxide, cumene hydroperoxide, dilauroyl peroxide or azo initiators, e.g. azodiisobutyronitrile (AIBN), may be used. Likewise suitable are inorganic peroxy compounds, e.g. $(NH_4)_2S_2O_8$, $K_2S_2O_8$ or $H_2O_2$, optionally in combination with reducing agents (e.g. sodium hydrogensulfite, ascorbic acid, iron(II) sulfate, etc.) or redox systems which contain an aliphatic or aromatic sulfonic acid (e.g. benzenesulfonic acid, toluenesulfonic acid, etc.) as the reducing component.

Useful polymerization media may be any solvents which behave very substantially inertly with respect to free-radical polymerization reactions and permit the formation of high molecular weights. Preference is given to using water and lower, tertiary alcohols or hydrocarbons having from 3 to 30 carbon atoms. In a particularly preferred embodiment, the reaction medium used is t-butanol. Mixtures of two or more representatives of the potential solvents described are of course likewise in accordance with the invention. This also includes emulsions of mutually immiscible solvents (e.g. water/hydrocarbons). In principle, all types of reaction are suitable which lead to the inventive polymer structures (for example solution polymerization, precipitation methods, suspension methods).

Precipitation polymerization is preferably suitable, more preferably precipitation polymerization in tert-butanol.

The list which follows shows 69 copolymers which are preferably present in the inventive concentrates.

Polymers having hydrophobic side chains, uncrosslinked

| No. | Composition | Preparation process |
|---|---|---|
| 1 | 95 g AMPS ® 5 g Genapol T-080 methacrylate | 1 |
| 2 | 90 g AMPS ® 10 g Genapol T-080 methacrylate | 1 |
| 3 | 85 g AMPS ® 15 g Genapol T-080 methacrylate | 1 |
| 4 | 80 g AMPS ® 20 g Genapol T-080 methacrylate | 1 |
| 5 | 70 g AMPS ® 30 g Genapol T-080 methacrylate | 1 |
| 6 | 50 g AMPS ® 50 g Genapol T-080 methacrylate | 1, 2 |
| 7 | 40 g AMPS ® 60 g Genapol T-080 methacrylate | 2 |
| 8 | 30 g AMPS ® 70 g Genapol T-080 methacrylate | 2 |
| 9 | 20 g AMPS ® 80 g Genapol T-080 methacrylate | 2 |
| 10 | 60 g AMPS ® 60 g BB10 acrylate | 1 |
| 11 | 80 g AMPS ® 20 g BB10 acrylate | 1 |
| 12 | 90 g AMPS ® 10 g BB10 methacrylate | 1 |
| 13 | 80 g AMPS ® 20 g BB10 methacrylate | 1 |
| 14 | 80 g AMPS ® 20 g Genapol LA040 acrylate | 1 |

Polymers having hydrophobic side chains, crosslinked

| No. | Composition | Preparation process |
|---|---|---|
| 15 | 80 g AMPS ® 20 g Genapol LA040 methacrylate 0.6 g AMA | 1 |
| 16 | 80 g AMPS ® 20 g Genapol LA040 methacrylate 0.8 g AMA | 1 |
| 17 | 80 g AMPS ® 20 g Genapol LA040 methacrylate 1.0 g AMA | 1 |
| 18 | 628.73 g AMPS ® 120.45 g Genapol T-250 acrylate 6.5 g TMPTA | 2 |
| 19 | 60 g AMPS ® 40 g BB10 acrylate 1.9 g TMPTA | 1, 2 |
| 20 | 80 g AMPS ® 20 g BB10 acrylate 1.4 g TMPTA | 1 |
| 21 | 90 g AMPS ® 10 g BB10 methacrylate 1.9 g TMPTA | 1 |
| 22 | 80 g AMPS ® 20 g BB25 methacrylate 1.9 g TMPTA | 1 |
| 23 | 60 g AMPS ® 40 g BB10 acrylate 1.4 g TMPTA | 1 |

Polymers having hydrophobic side chains, crosslinked, grafted

| No. | Composition | Preparation process |
|---|---|---|
| 24 | 95 g AMPS ® 5 g BB10 acrylate, 1.9 g TMPTA, 1 g Poly-NVP | 1 |
| 25 | 90 g AMPS ® 10 g BB10 acrylate, 1.9 g TMPTA, 1 g Poly-NVP | 1 |
| 26 | 85 g AMPS ® 15 g BB10 acrylate, 1.9 g TMPTA, 1 g Poly-NVP | 1 |
| 27 | 90 g AMPS ® 10 g BB10 methacrylate, 1.9 g TMPTA, 1 g Poly-NVP | 1 |

Polymers having silicon-containing groups, uncrosslinked

| No. | Composition | Preparation process |
|---|---|---|
| 28 | 80 g AMPS ®, 20 g Silvet 867 | 1 |
| 29 | 80 g AMPS ®, 50 g Silvet 867 | 1, 2 |

Polymers having silicon-containing groups, crosslinked

| No. | Composition | Preparation process |
|---|---|---|
| 30 | 80 g AMPS ®, 20 g Silvet 867, 0.5 g MBA | 1 |
| 31 | 80 g AMPS ®, 20 g Silvet 867, 1.0 g MBA | 1 |
| 32 | 60 g AMPS ®, 40 g Y-12867, 0.95 g AMA | 1 |
| 33 | 80 g AMPS ®, 20 g Y-12867, 0.95 g AMA | 1 |
| 34 | 90 g AMPS ®, 10 g Y-12867, 0.95 g AMA | 1 |
| 35 | 60 g AMPS ®, 40 g Silvet 7280, 0.95 g AMA | 1, 2 |
| 36 | 80 g AMPS ®, 20 g Silvet 7280, 0.95 g AMA | 1 |
| 37 | 90 g AMPS ®, 10 g Silvet 7280, 0.95 g AMA | 1 |
| 38 | 60 g AMPS ®, 40 g Silvet 7608, 0.95 g AMA | 1, 2 |
| 39 | 80 g AMPS ®, 20 g Silvet 7608, 0.95 g AMA | 1 |
| 40 | 90 g AMPS ®, 10 g Silvet 7608, 0.95 g AMA | 1 |

Polymers having hydrophobic side chains and cationic groups, uncrosslinked

| No. | Composition | Preparation process |
|---|---|---|
| 41 | 87.5 g AMPS ®, 7.5 g Genapol T-110, 5 g DADMAC | 1 |
| 42 | 40 g AMPS ®, 10 g Genapol T110, 45 g methacrylamide | 1 |
| 43 | 55 g AMPS ®, 40 g Genapol LA040, 5 g Quat | 1 |
| 44 | 75 g AMPS ®, 10 g BB10, 6.7 g Quat | 1 |

Polymers having hydrophobic side chains and cationic groups, crosslinked

| No. | Composition | Preparation process |
|---|---|---|
| 45 | 60 g AMPS ®, 20 g Genapol T-80, 10 g Quat, 10 g HEMA | 1 |
| 46 | 75 g AMPS ®, 20 g Genapol T-250, 5 g Quat, 1.4 g TMPTA | 1 |
| 47 | 75 g AMPS ®, 20 g Genapol T-250, 10 g Quat, 1.4 g TMPTA | 1 |
| 48 | 75 g AMPS ®, 20 g Genapol T-250, 20 g Quat, 1.4 g TMPTA | 1 |

Polymers having fluorine-containing groups

| No. | Composition | Preparation process |
|---|---|---|
| 49 | 94 g AMPS ®, 2.02 g Fluowet AC 600 | 1 |
| 50 | 80 g AMPS ®, 20 g perfluorooctyl polyethylene glycol methacrylate | 1 |

Polymers having fluorine-containing groups, grafted

| No. | Composition | Preparation process |
|---|---|---|
| 51 | 80 g AMPS ®, 10 g Fluowet AC 600, 5 g Poly-NVP | 1 |
| 52 | 70 g AMPS ®, 8 g perfluorooctylethyloxyglycerol methacrylate, 5 g Poly-NVP | 1 |

Multifunctional polymers

| No. | Composition | Preparation process |
|---|---|---|
| 53 | 80 g AMPS ®, 10 g Genapol LA070, 10 g Silvet 7608, 1.8 g TMPTA | 1 |
| 54 | 70 g AMPS ®, 5 g N-vinylpyrrolidone, 15 g Genapol T-250 methacrylate, 10 g Quat, 10 g Poly-NVP | 1 |
| 55 | 80 g AMPS ®, 5 g N-vinylformamide, 5 g Genapol O-150 methacrylate, 10 g DADMAC, 1.8 g TMPTA, 8 g Poly-N-vinylformamide | 1 |
| 56 | 70 g AMPS ®, 5 g N-vinylpyrrolidone, 15 g Genapol T-250 methacrylate, 10 g Quat, 10 g Poly-NVP | 1 |

-continued

| No. | Composition | Preparation process |
|---|---|---|
| 57 | 60 g AMPS ®, 10 g Genapol-BE-020 methacrylate, 10 g Genapol T-250 acrylate, 20 g Quat, | 1 |
| 58 | 60 g AMPS ®, 20 g MPEG-750 methacrylate, 10 g methacryloyloxypropyldimethicone, 10 g perfluorooctyl polyethylene glycol methacrylate, 10 g poly[N-vinylcaprolactone-co-acrylic acid] (10/90) | 1 |
| 59 | 80 g AMPS ®, 5 g N-vinylformamide, 5 g Genapol O-150 methacrylate, 10 g DADMAC, 1.8 g TMPTA | 1 |
| 60 | 70 g AMPS ®, 10 g Genapol T-250 acrylate, 5 g N-methyl-4-vinylpyridinium chloride, 2.5 g Silvet Y-12867, 2.5 g perfluorohexyl polyethylene glycol methacrylate, 10 g polyethylene glycol dimethacrylate, 4 g poly[N-vinylcaprolactam] | 1 |
| 61 | 10 g AMPS ®, 20 g acrylamide, 30 g N-2-vinylpyrrolidone, 20 g Silvet 7608, 10 g methacryloyloxypropyldimethicone, 10 g Fluowet AC 812 | 2 |
| 62 | 60 g AMPS ®, 10 g DADMAC, 10 g Quat, 10 g Genapol-LA-250 crotonate, 10 g methacryloyloxypropyldimethicone, 7 g poly[acrylic acid-co-N-vinylformamide] | 1 |
| 63 | 50 g AMPS ®, 45 g Silvet 7608, 1.8 g TMPTA, 8 g poly[N-vinylformamide] | 1, 2 |
| 64 | 20 g AMPS ®, 10 g Genapol T 110, 35 g MAA, 30 g HEMA, 5 g DADMAC | 2 |
| 65 | 20 g AMPS ®, 80 g BB10, 1.4 g TMPTA | 2 |
| 66 | 75 g AMPS ®, 20 g BB10, 6.7 g Quat, 1.4 g TMPTA | 1 |
| 67 | 35 g AMPS ®, 60 g acrylamide, 2 g VIFA, 2.5 g vinylphosphonic acid, 2 mol % Fluowet EA-600 | 1 |
| 68 | 20 g AMPS ®, 80 g BB10 methacrylate, | 2 |
| 69 | 5 g AMPS ®, 95 g LA 070 methacrylate | 2 |

The copolymers No. 1 to No. 69 can be synthesized in accordance with the following preparation methods 1 or 2.

Method 1:

This method is suitable for polymers which can be prepared in precipitation methods in an organic medium (preferably t-butanol, aqueous t-butanol). In this method, the monomers are initially charged in the appropriate solvent, optionally neutralized and subsequently polymerized by adding an initiator. The resulting polymer suspension is stirred for sufficiently long to complete the reaction and to minimize the residual monomer concentration. In the case of low-boiling organic media, the continued stirring phase is carried out in the heat of boiling. On completion of reaction, the later liquid medium and all assistants are added with stirring to the polymer suspension and the lower-boiling former polymerization medium is subsequently removed by distillation. To complete the removal and for more gentle workup, it is possible to work under reduced pressure. On completion of removal, the polymer suspension is stirred further, optionally with the supply of heat and/or addition of further ingredients (for example water, active substances, etc.), until the desired consistency and performance is achieved.

Method 2:

This method is suitable for polymers which can be prepared in solution methods in an organic medium (preferably t-butanol, aqueous t-butanol). In this method, the monomers are initially charged in the appropriate solvent, optionally neutralized and subsequently polymerized by adding an initiator. The resulting polymer solution is stirred for sufficiently long to complete the reaction and to minimize the residual monomer concentration. In the case of low-boiling organic media, the continued stirring phase is carried out in the heat of boiling. On completion of reaction, the later liquid medium and all assistants are added with stirring to the polymer solution and the lower-boiling former polymerization medium is subsequently removed by distillation. To complete the removal and for more gentle workup, it is possible to work under reduced pressure. On completion of removal, the polymer solution is stirred further, optionally with the supply of heat and/or addition of further ingredients (for example water, active substances, etc.), until the desired consistency and performance is achieved.

Chemical naming of the commercial products used:

| | |
|---|---|
| AMPS ® | Acryloyldimethyltaurate, either Na or $NH_4$ salt (AMPS ® is a product from The Lubrizol Company) |
| Genapol ® T-080 | $C_{16}$–$C_{18}$ fatty alcohol polyglycolether having 8 EO units |
| Genapol ® T-110 | $C_{12}$–$C_{14}$ fatty alcohol polyglycolether having 11 EO units |
| Genapol ® T-250 | $C_{16}$–$C_{18}$ fatty alcohol polyglycolether having 25 EO units |
| Genapol ® LA-040 | $C_{12}$–$C_{14}$ fatty alcohol polyglycolether having 4 EO units |
| Genapol ® LA-070 | $C_{12}$–$C_{14}$ fatty alcohol polyglycolether having 7 EO units |
| Genapol ® O-150 methacrylate | $C_{16}$–$C_{18}$-fatty alcohol polyglycolether Methacrylate having 15 EO units, |
| Genapol ® LA-250 crotonate | $C_{12}$–$C_{14}$ fatty alcohol polyglycolether crotonate having 25 EO units |
| Genapol ® T-250 methacrylate | $C_{16}$–$C_{18}$ fatty alcohol polyglycolether methacrylate having 25 EO units |
| Genapol ® T-250 acrylate | $C_{16}$–$C_{18}$ fatty alcohol polyglycolether methacrylate having 25 EO units |
| BB10 ® | Polyoxyethylene(10) behenyl ether |
| TMPTA | Trimethylolpropane triacrylate |
| Poly-NVP | Poly-N-vinylpyrrolidone |
| Silvet ® 867 | Siloxane-polyalkylene oxide copolymer |
| MBA | Methylenebisacrylamide |
| AMA | Allyl methacrylate |
| ® Y-12867 | Siloxane-polyalkylene oxide copolymer |
| Silvet ® 7608 heptamethyltrisiloxane | Polyalkylene oxide-modified |
| Silvet ® 7280 | Polyalkylene oxide-modified heptamethyltrisiloxane |
| DADMAC | Diallyldimethylammonium chloride |
| HEMA | 2-Hydroxyethyl methacrylate |
| Quat | 2-(Methacryloyloxy)ethyltrimethylammonium chloride |
| Fluowet ® AC 600 | Perfluoroalkylethyl acrylate |
| Span ® 80 | Sorbitan ester |

The described grafting of the copolymers with other polymers which can optionally be carried out leads to products having particular polymer morphology which result in optically clear gels in aqueous systems. A potential disadvantage of the copolymers without grafting consists in more or less intense opalescence in aqueous solution. This is based on hitherto unavoidable overcrosslinked polymer fractions which are formed during the synthesis and are present in water swollen only inadequately. This results in light-scattering particles forming, whose size is distinctly above the wavelength of visible light and is therefore the consequence of the opalescence. The described grafting method which is optionally carried out distinctly reduces or completely prevents the formation of overcrosslinked polymer particles compared to conventional techniques. The described optional incorporation either of cationic charges or of silicon, fluorine or phosphorus atoms into the polymers leads to products which have particular sensory and rheological properties in cosmetic formulations. An improvement in the sensory and rheological properties may be desired, especially in the case of use in rinse-off products (especially hair treatment compositions) and also leave-on products (especially O/W emulsions).

In addition to the polymer, the inventive concentrates comprise an organic solvent or solvent mixture whose boiling point is at least 10° C. higher than the polymerization medium used, preferably oils from the group of the hydrocarbons, ester oils, vegetable oils and silicone oils.

The oils used in accordance with the invention include hydrocarbon oils having linear or branched, saturated or unsaturated $C_7$-$C_{40}$ hydrocarbon chains, for example Vaseline, dodecane, isododecane, cholesterol, lanolin, hydrogenated polyisobutylenes, docosanes, hexadecane, isohexadecane, paraffins and isoparaffins; oils of vegetable origin, especially liquid triglycerides such as sunflower oil, corn oil, soya oil, rice oil, jojoba oil, babusscu oil, pumpkin oil, grapeseed oil, sesame oil, walnut oil, apricot oil, macadamia oil, avocado oil, sweet almond oil, meadowfoam oil, castor oil, olive oil, peanut oil, rapeseed oil and coconut oil; oils of animal origin, e.g. beef tallow, pork lard, goose lard, perhydrosqualene, lanolin; synthetic oils such as purcellin oil, isoparaffin, linear and/or branched fatty alcohols and fatty acid esters, preferably Guerbet alcohols having from 6 to 18, preferably from 8 to 10, carbon atoms; ester of linear ($C_6$-$C_{13}$) fatty acids with linear ($C_6$-$C_{20}$) fatty alcohols; esters of branched ($C_6$-$C_{13}$) carboxylic acids with linear ($C_6$-$C_{20}$) fatty alcohols, esters of linear ($C_6$-$C_{18}$) fatty acids with branched alcohols, especially 2-ethylhexanol; esters of linear and/or branched fatty acids with polyhydric alcohols (for example dimer diol or trimer diol) and/or Guerbet alcohols; alcohol esters of $C_1$-$C_{10}$-carboxylic acids or $C_2$-$C_{30}$-dicarboxylic acids, $C_1$-$C_{30}$-carboxylic monoesters and polyesters of sugar, $C_1$-$C_{30}$-monoesters and polyesters of glycerol; waxes such as beeswax, paraffin wax or microwaxes, optionally in combination with hydrophilic waxes, for example cetylstearyl alcohol; fluorinated and perfluorinated oils; monoglycerides of $C_1$-$C_{30}$-carboxylic acids, diglycerides of $C_1$-$C_{30}$-carboxylic acids, triglycerides of $C_1$-$C_{30}$-carboxylic acids, for example triglycerides of caprylic/capric acids, ethylene glycol monoesters of $C_1$-$C_{30}$-carboxylic acids, ethylene glycol diesters of $C_1$-$C_{30}$-carboxylic acids, propylene glycol monoesters of $C_1$-$C_{30}$-carboxylic acids, propylene glycol diesters of $C_1$-$C_{30}$-carboxylic acids, and also propoxylated and ethoxylated derivatives of the abovementioned compound classes.

Useful silicone oils include dimethylpolysiloxanes, cyclomethicones, polydialkylsiloxanes $R_3SiO(R_2SiO)_x SiR_3$, where R is methyl or ethyl, more preferably methyl, and x is a number from 2 to 500, for example the dimethicones obtainable under the trade names VICASIL (General Electric Company), DOW CORNING 200, DOW CORNING 225, DOW CORNING 200 (Dow Corning Corporation), trimethylsiloxysilicates $[(CH_2)_3SiO)_{1/2}]_x[SiO_2]_y$, where x is a number from 1 to 500 and y is a number from 1 to 500, dimethiconols $R_3SiO[R_2SiO]_xSiR_2OH$ and $HOR_2SiO[R_2SiO]_xSiR_2OH$, where R is methyl or ethyl and x is a number up to 500, polyalkylarylsiloxanes, e.g. the polymethylphenylsiloxanes obtainable under the trade names SF 1075 METHYLPHENYL FLUID (General Electric Company) and 556 COSMETIC GRADE PHENYL TRIMETHICONE FLUID (Dow Corning Corporation), polydiarylsiloxanes, silicone resins, cyclic silicones, and amino-, fatty acid-, alcohol-, polyether-, epoxy-, fluorine- and/or alkyl-modified silicone compounds, and also polyethersiloxane copolymers, as described in U.S. Pat. No. 5,104,645 and the references cited therein, which may be either in liquid form or resin form at room temperature.

The inventive concentrates may optionally contain emulsifiers and/or water.

Useful emulsifiers include addition products of from 0 to 30 mol of alkylene oxide, in particular ethylene oxide, propylene oxide, butylene oxide, to linear fatty alcohols having from 8 to 22 carbon atoms, to fatty acids having from 12 to 22 carbon atoms, to alkylphenols having from 8 to 15 carbon atoms in the alkyl group and to sorbitan esters; ($C_{12}$-$C_{18}$) fatty acid mono- and diesters of addition products of from 0 to 30 mol of ethylene oxide to glycerol; glycerol mono- and diesters and sorbitan mono- and diesters of saturated and unsaturated fatty acids having from 6 to 22 carbon atoms and in some cases their ethylene oxide addition products; addition products of from 15 to 60 mol of ethylene oxide to castor oil and/or hardened castor oil; polyol and in particular polyglycerol esters, for example polyglycerol polyricinoleate and polyglycerol poly-12-hydroxystearate. Preference is given to liquid fatty acid esters which may either be ethoxylated (PEG-10 polyglyceryl-2 laurates) or nonethoxylated (polyglyceryl-2 sesquiisostearates).

Further inventive concentrates preferably contain sorbitol esters prepared by reacting sorbitol with fatty acid methyl esters or fatty acid triglycerides. The fatty acid radical in the fatty acid methyl esters and fatty acid triglycerides generally contains from 8 to 22 carbon atoms and may be straight-chain or branched, saturated or unsaturated. Examples thereof are palmitic acid, stearic acid, lauric acid, linoleic acid, linolenic acid, isostearic acid or oleic acid. Useful fatty acid triglycerides include all natural animal or vegetable oils, fats and waxes, for example olive oil, rapeseed oil, palm kernel oil, sunflower oil, coconut oil, linseed oil, castor oil, soybean oil, optionally also in refined or hydrogenated form. Since these natural fats, oils and waxes are normally mixtures of fatty acids having differing chain lengths, this also applies to the fatty acid radicals in the sorbitol esters used in accordance with the invention. The sorbitol esters used in accordance with the invention may also be alkoxylated, preferably ethoxylated.

In addition, anionic emulsifiers such as ethoxylated and nonethoxylated mono-, di- or triphosphoric esters, but also cationic emulsifiers such as mono-, di- and trialkylquats and their polymeric derivatives may also be used.

Likewise suitable are mixtures of compounds of a plurality of these substance classes.

The inventive concentrates are outstandingly suitable as thickeners, bodying agents, emulsifiers, solubilizers, dispersants, lubricants, adhesives, conditioners and/or stabilizers for formulating cosmetic, pharmaceutical and dermatological compositions, in particular of oil-in-water emulsions in the form of creams, lotions, cleansing milk, cream gels, spray emulsions, for example body lotions, aftersun lotions, sunscreens and deodorant sprays.

The invention therefore also provides cosmetic, pharmaceutical and dermatological preparations comprising a concentrate which has been prepared by the process according to the invention.

The inventive concentrates are used in the cosmetic and pharmaceutical preparations in amounts by weight which result in polymer concentrations of from 0.01 to 10% by weight, preferably from 0.1 to 5% by weight, more preferably from 0.5 to 3% by weight, based on the finished compositions.

The inventive compositions may contain anionic, cationic, nonionic, zwitterionic and/or amphoteric surfactants, and also further assistants and additives, cationic polymers, film formers, superfatting agents, stabilizers, active biogenic ingredients, glycerol, preservatives, pearlizing agents, colorants and fragrances, solvents, opacifiers, and also protein derivatives such as gelatin, collagen hydrolysates, natural- and synthetic-based polypeptides, egg yolk, lecithin, lanolin and lanolin derivatives, fatty alcohols, silicones, deodorizing agents, substances having keratolytic and keratoplastic action, enzymes and carrier substances. In addition, agents having antimicrobial action may be added to the inventive compositions.

In addition, the inventive compositions may contain organic solvents. In principle, useful organic solvents are all mono- or polyhydric alcohols. Preference is given to alcohols having from 1 to 4 carbon atoms such as ethanol, propanol, isopropanol, n-butanol, i-butanol, t-butanol, glycerol and mixtures of the alcohols mentioned. Further preferred alcohols are polyethylene glycols having a relative molecular mass below 2000. Particular preference is given to using polyethylene glycol having a relative molecular mass between 200 and 600 in amounts of up to 45% by weight, and polyethylene glycol having a relative molecular mass between 400 and 600 in amounts of from 5 to 25% by weight. Further suitable solvents are, for example, triacetin (glycerol triacetate) and 1-methoxy-2-propanol. Short-chain anionic surfactants, especially arylsulfonates, for example cumenesulfonate or toluene-sulfonate, have hydrotropic action.

The examples which follow are intended to illustrate the subject matter of the invention in detail, without restricting it thereto (the percentages are percentages by weight).

Various base formulations having a high emulsifier concentration (A1 to A6), having a low emulsifier concentration (B1 to B6) and also without emulsifier ($C_1$ and $C_2$) were prepared. In each case, various polymers from the above tables were prepared:

Polymer No. 1, 4: (low modification, uncrosslinked)
Polymer No. 17, 18, 22: (low modification, crosslinked)
Polymer No. 41, 44: (low modification, cationic, uncrosslinked)
Polymer No. 68, 69: (high modification, uncrosslinked)

EXAMPLE A4

Polymer Concentrate Having High Emulsifier Fraction

A 1 l flat-flange flask equipped with temperature sensor, reflux condenser, precision glass stirrer and pH control is initially charged at 30° C. with 395 g of t-butanol, 5 g of isopropanol and 80 g of acryloyldimethyltaurine. Subsequently, neutralization is effected by introducing gaseous ammonia, and the required amount of macromonomer (laureth-7 methacrylate) and 1.5 g of trimethylolpropane triacrylate (crosslinker) is added to the reaction mixture. The reaction mixture is subsequently inertized by introducing $N_2$ and heated to 60° C., and the reaction is initiated after 30 minutes by adding 1 g of dilauroyl peroxide. This results in an exothermic reaction in which the interior temperature rises by several degrees. After about 10 minutes, the polymer being formed precipitates, which becomes noticeable in a constant rise in the solution viscosity. After completion of the exothermic phase (about 20-30 minutes), the reaction mixture is heated to boiling and boiled for a further 2 hours to complete the reaction. During this time, the viscosity of the solution falls again. Afterwards, the reflux condenser is replaced by a distillation head with condenser. 71 g of Hostacerin DGI, 105 g of Hostaphat KL 340D and 44 g of Myrithol 318 are now added to the polymer suspension and the majority of t-butanol is subsequently removed by distillation with good stirring. Application of a vacuum removes the residues of the reaction butanol from the mixture. Care has to be taken that the vacuum applied does enable the removal by distillation of the t-butanol, but the corresponding boiling temperature of the solvent at this pressure is not exceeded. Once the removal of the t-butanol has been completed, the mixture is cooled and the product discharged from the flask.

The polymer concentrates A1 to A3 and A5 and A6 are prepared in a similar manner.

EXAMPLE B6

Polymer Concentrate Having Low Emulsifier Fraction

A 1 l flat-flange flask equipped with temperature sensor, reflux condenser, precision glass stirrer and pH control is initially charged at 30° C. with 400 g of t-butanol 90 g of acryloyldimethyltaurine. Subsequently, neutralization is effected by introducing gaseous ammonia, and 15 g of N-vinylpyrrolidone, 4 g of laureth-7 methacrylate and 5 g of beheneth-25 methacrylate are added to the reaction mixture. The reaction mixture is subsequently inertized by introducing $N_2$ and heated to 60° C., and the reaction is initiated after 30 minutes by adding 1 g of dilauroyl peroxide. This results in an exothermic reaction in which the interior temperature rises by several degrees. After about 10 minutes, the polymer being formed precipitates, which becomes noticeable in a constant rise in the solution viscosity. After completion of the exothermic phase (about 20-30 minutes), the reaction mixture is heated to boiling and boiled for a further 2 hours to complete the reaction. During this time, the viscosity of the solution falls again. Afterwards, the reflux condenser is replaced by a distillation head with condenser. 8.3 g of Hostacerin DGI, 5.5 g of Hostaphat KL 340D, 82 g of paraffin and 82 g of isopropyl palmitate are now added to the polymer suspension and the majority of t-butanol is subsequently removed by distillation with good stirring. Application of a vacuum removes the residues of the reaction butanol from the mixture. Care has to be taken that the vacuum applied does enable the removal by distillation of the t-butanol, but the corresponding boiling temperature of the solvent at this pressure is not exceeded. Once the removal of the t-butanol has been completed, the mixture is cooled and the product discharged from the flask.

The polymer concentrates B1 to B5 are prepared in a similar manner.

EXAMPLE C1

Polymer Concentrate Without Emulsifier

A 1 l flat-flange flask equipped with temperature sensor, reflux condenser, precision glass stirrer and pH control is initially charged at 30° C. with 400 g of t-butanol and 30 g of acryloyldimethyltaurine. Subsequently, neutralization is effected by introducing gaseous ammonia, and the required amount of macromonomer (70 g of beheneth-25 methacrylate) is added to the reaction mixture. The reaction mixture is subsequently inertized by introducing $N_2$ and heated to 60° C., and the reaction is initiated after 30 minutes by adding 1 g of dilauroyl peroxide. This results in an exothermic reaction in which the interior temperature rises by several degrees. On completion of this phase (about 20-30 minutes), the reaction solution is heated to boiling and boiled for a further 2 hours to complete the reaction. Subsequently, the reflux condenser is replaced by a distillation head with condenser and the majority of t-butanol is removed by distillation. 178 g of Myrithil 318 (corresponds later to 64% by weight) are added to the polymer concentrate. This completely dissolves the polymer in the solvent. Application of a vacuum removes the residues of the reaction butanol from the mixture. Care has to be taken that the vacuum applied does enable the removal by distillation of the t-butanol, but the corresponding boiling temperature of the solvent at this pressure is not exceeded. Once the removal of the t-butanol has been completed, the mixture is cooled and the product discharged from the flask.

The polymer concentrate C2 is prepared in a similar manner.

The resulting polymer concentrates were assessed by appearance, viscosity and stability (sedimentation on storage at 25° C. for 3 weeks).

TABLE 1

Polymer concentrates A1–A6, B1–B6, C1 and C2

1. High emulsifier

| concentration | Polymer No. 18 A1 | 22 A2 | 17 A3 | 41 A4 | 22 A5 | 22 A6 |
|---|---|---|---|---|---|---|
| Polymer | 36.0% | 36.0% | 36.0% | 36.0% | 36.0% | 36% |
| Hostacerin DGI | 25.6% | 12.8% | 51.2% | 25.6% | 28.8% | 30% |
| Hostaphat KL 340 D | 6.4% | 19.2% | 12.8% | 38.4% | 19.2% | 18% |
| Myritol 318 | 32.0% | 32.0% | 0.0% | 16.0% | 24.0% | 16% |
| Paraffin | 0.0% | 0.0% | 0.0% | 0.0% | 0.0% | 0.0% |
| IPP | 0.0% | 0.0% | 0.0% | 0.0% | 0.0% | 0.0% |

2. Low emulsifier

| concentration | Polymer No. 1 B1 | 4 B2 | 44 B3 | 18 B4 | 22 B5 | 22 B6 |
|---|---|---|---|---|---|---|
| Polymer | 36.0% | 36.0% | 36.0% | 36.0% | 36.0% | 36% |
| Hostacerin DGI | 4.0% | 2.0% | 4.0% | 2.0% | 3.0% | 3% |
| Hostaphat KL 340 D | 1.0% | 3.0% | 1.0% | 3.0% | 2.0% | 2% |
| Myritol 318 | 59.0% | 59.0% | 0.0% | 0.0% | 29.5% | 0.0% |
| Paraffin | 0.0% | 0.0% | 59.0% | 59.0% | 29.5% | 29.5% |
| IPP | 0.0 | 0.0 | 0.0 | 0.0 | 0.0 | 29.5 |

3. Without emulsifier

| | Polymer No. 68 C1 | 69 C2 |
|---|---|---|
| Polymer | 36.0% | 36.0% |
| Hostacerin DGI | 0.0% | 0.0% |
| Hostaphat KL 340 D | 0.0 | 0.0 |
| Myritol 318 | 64.0% | 59.0% |
| Paraffin | 0.0% | 5.0% |
| IPP | 0.0 | 0.0 |

Appearance:

A1-A6, B1-B6: dispersions, pourable (viscosity<10 000 mPas) C1, C2: transparent solutions, pourable (viscosity<10 000 mPas) Chemical description of the commercial products used:

| Hostacerin DGI | Polyglyceryl-2 Sesquiisostearate |
| Myritol 318 | Caprylic/Capric Triglyceride |
| IPP | Isopropyl palmitate |
| Hostaphat KL340D | Trilaureth-4 Phosphate |

What is claimed is:

1. A process for preparing a concentrate in liquid or liquid-disperse form, comprising
I) from 5 to 80% by weight of a polymer obtainable by free-radically polymerizing acryloyldimethyltaurine, acryloyldimethyltaurates or mixtures thereof in the presence of one or more substances selected from one or more of the components D) to G),
    D) consisting of at least monofunctional silicon-containing substances capable of free-radical polymerization;
    E) consisting of at least monofunctional fluorine-containing substances capable of free-radical polymerization,
    F) consisting of olefinically mono- or polyunsaturated, optionally crosslinking macromonomers which each have at least one oxygen, nitrogen, sulfur or phosphorus atom and a number-average molecular weight greater than or equal to 200 g/mol, the macromonomers not being silicon-containing substances as per component D) or fluorine-containing substances as per component E), and
    G) consisting of polymeric additives having number-average molecular weights of from 200 g/mol to $10^9$ g/mol,
II) from 20 to 95% by weight of an organic solvent or solvent mixture,
III) from 0 to 60% by weight of an emulsfier, and
IV) from 0 to 30% by weight of water,
comprising the steps of:
    a) polymerizing acryloyldimethyltaurine, acryloyldimethyltaurates or mixtures thereof in the presence of at least one substance or a plurality of substances selected from one or more of the components D) to G) by a free-racical polymerization reaction in a polymerization medium which behaves inertly with respect to free-radical polymerization reactions and permits the formation of high molecular weights,
    b) subsequently adding a higher-boiling solvent or solvent mixture, to the mixture of polymer and polymerization medium obtained from step a), the boiling point of the higher-boiling solvent or solvent mixture added being at least 10° C. higher than that of the polymerization medium used for the polymerization, and
    c) subsequently removing the polymerization medium.

2. The process as claimed in claim 1, wherein the polymerizing step further comprises polymerizing in the presence of one or more more further substances.

3. The process as claimed in claim 2, wherein the one or more further substances are selected from the group consisting of further at least monofunctional comonomers capable of free-radical polymerization and polymeric additives.

4. The process as claimed in claim 3, wherein the further substances are comonomers capable of free-radical polymerization and are selected from the group consisting of:
    a) olefinically unsaturated, noncationic, optionally crosslinking comonomers which have at least one oxygen, nitrogen, sulfur or phosphorus atom and have a molecular weight of less than 500 g/mol, and
    b) olefinically unsaturated, cationic comonomers which have at least one oxygen, nitrogen, sulfur or phosphorus atom and a molecular weight of less than 500 g/mol.

5. The process as claimed in claim 1, wherein the polymer present in the concentrate contains from 20 to 99.5% by weight, based on the total mass of the polymer, of acryloyldimethyltaurine, acryloyldimethyltaurates or mixtures thereof.

6. The process as claimed in claim 1, wherein the concentrate contains from 20 to 60% by weight of polymer, based on the total mass of the concentrate.

7. The process as claimed in claim 6, wherein the concentrate contains from 30 to 40% by weight of polymer, based on the total mass of the concentrate.

8. The process for preparing a concentrate as claimed in. claim 1, wherein the concentrate contains from 30 to 80% by weight, based on the total mass of the concentrate, of solvent or solvent mixture, or solvent or solvent mixture and emulsifier.

9. The process as claimed in claim 8, wherein the concentrate contains from 40 to 60% by weight, based on the total mass of the concentrate, of solvent or solvent mixture, or solvent or solvent mixture and emulsifier.

10. The process as claimed in claim 1, wherein the concentrate contains from 0 to 10% by weight of water, based on the total mass of the concentrate.

11. The process as claimed in claim 10, wherein the concentrate contains from 0 to 5% by weight of water, based on the total mass of the concentrate.

12. The process as claimed in claim 1, wherein said adding step further comprises adding an emulsifier, water or both to the mixture of polymer and polymerization medium.

13. The process as claimed in claim 1, wherein the removing step further comprises removing the polymerization medium at a pressure lower than atmospheric temperature.

14. The process as claimed in claim 1, wherein the concentrate contains 0% by weight of water, based on the total mass of the concentrate.

15. The process as claimed in claim 1, wherein the concentrate contains
   II) from 30 to 80% by weight of an organic solvent or solvent mixture,
   III) 0% by weight of an emulsifier, and
   IV) from 0 to 10% by weight of water, based on the total mass of the concentrate.

16. The process as claimed in claim 1, wherein the concentrate contains
   II) from 40 to 80% by weight of an organic solvent or solvent mixture,
   III) 0% by weight of an emulsifier, and
   IV) 0% by weight of water, based on the total mass of the concentrate.

17. The process for preparing a concentrate in liquid or liquid-disperse form, according to claim 1, consisting of the steps of:
   a) polymerizing acryloyldimethyltaurine, acryloyldimethyltaurates or mixtures thereof in the presence of at least one substance or a plurality of substances selected from one or more of the components D) to G) by a free-radical polymerization reaction in a polymerization medium which behaves inertly with respect to free-radical polymerization reactions and permits the formation of high molecular weights,
   b) subsequently adding a higher-boiling solvent or solvent mixture, to the mixture of polymer and polymerization medium obtained from step a), the boiling point of the higher-boiling solvent or solvent mixture added being at least 10C. higher than that of the polymerization medium used for the polymerization, and
   c) subsequently removing the polymerization medium.

18. The process for preparing a concentrate in liquid or liquid-disperse form, according to claim 1, consisting of:
   I) from 5 to 80% by weight of a polymer obtainable by free-radically polymerizing acryloyldimethyltaurine, acryloyldimethyltaurates or mixtures thereof in the presence of one or more substances selected from one or more of the components D) to G),
      D) consisting of at least monofunctional silicon-containing substances capable of free-radical polymerization,
      E) consisting of at least monofunctional fluorine-containing substances capable of free-radical polymerization,
      F) consisting of olefinically mono- or polyunsaturated, optionally crosslinking macromonomers which each have at least one oxygen, nitrogen, sulfur or phosphorus atom and a number-average molecular weight greater than or equal to 200 g/mol, the macromonomers not being silicon-containing substances as per component D) or fluorine-containing substances as per component E), and
      G) consisting of polymeric additives having number-average molecular weights of from 200 g/mol to $10^9$ g/mol, and
   II) from 20 to 95% by weight of an organic solvent or solvent mixture.

19. The process for preparing a concentrate in liquid or liquid-disperse form, according to claim 14, consisting of:
   I) from 5 to 80% by weight of a polymer obtainable by free-radically polymerizing acryloyldimethyltaunne, acryloyldimethyltaurates or mixtures thereof in the presence of one or more substances selected from one or more of the components D) to G),
      D) consisting of at least monofunctional silicon-containing substances capable of free-radical polymerization,
      E) consisting of at least monofunctional fluorine-containing substances capable of free-radical polymerization.
      F) consisting of olefinically mono- or polyunsaturated, optionally crosslinking macromonomers which each have at least one oxygen, nitrogen, sulfur or phosphorus atom and a number-average molecular weight greater than or equal to 200 g/mol, the macromonomers not being silicon-containing substances as per component D) or fluorine-containing substances as per component E), and
      G) consisting of polymeric additives having number-average molecular weights of from 200 g/mol to $10^9$ g/mol, and
   II) from 20 to 95% by weight of an organic solvent or solvent mixture.

20. The process for preparing a concentrate in liquid or liquid-disperse form, according to claim 15, consisting of:
   I) from 5 to 80% by weight of a polymer obtainable by free-radically polymerizing acryloyldimethyltaurine, acryloyldimethyltaurates or mixtures thereof in the presence of one or more substances selected from one or more of the components D) to G),
      D) consisting of at least monofunctional silicon-containing substances capable of free-radical polymerization,
      E) consisting of at least monofunctional fluorine-containing substances capable of free-radical polymerization.
      F) consisting of olefinically mono- or polyunsaturated, optionally crosslinking macromonomers which each have at least one oxygen, nitrogen, sulfur or phosphorus atom and a number-average molecular weight greater than or equal to 200 g/mol, the macromonomers not being silicon-containing substances as per component D) or fluorine-containing substances as per component E), and
      G) consisting of polymeric additives having number-average molecular weights of from 200 g/mol to $10^9$ g/mol, and
   II) from 20 to 95% by weight of an organic solvent or solvent mixture.

21. The process for preparing a concentrate in liquid or liquid-disperse form, according to claim 16, consisting of:
   I) from 5 to 80% by weight of a polymer obtainable by free-radically polymerizing acryloyldimethyltaurine, acryloyldimethyltaurates or mixtures thereof in the presence of one or more substances selected from one or more of the components D) to G), D) consisting of at least monofunctional silicon-containing substances capable of free-radical polymerization, E) consisting of at least monofunctional fluorine-containing substances capable of free-radical polymerization, F) consisting of olefinically mono- or polyunsaturated, optionally crosslinking macromonomers which each have at least one oxygen, nitrogen, sulfur or phosphorus atom and a number-average molecular weight greater than or equal to 200 g/mol, the macromonomers not being silicon-containing substances as per component D) or fluorine-containing substances as per component E), and G) consisting of polymeric additives having number-average molecular weights of from 200 g/mol to $10^9$ g/mol, and II) from 20 to 95% by weight of an organic solvent or solvent mixture.

* * * * *